(12) United States Patent
Sherry

(10) Patent No.: US 7,192,441 B2
(45) Date of Patent: Mar. 20, 2007

(54) AORTIC ARTERY ANEURYSM ENDOVASCULAR PROSTHESIS

(75) Inventor: John E. Sherry, Needham, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/978,383

(22) Filed: Oct. 16, 2001

(65) Prior Publication Data
US 2003/0074058 A1 Apr. 17, 2003

(51) Int. Cl.
*A61F 2/06* (2006.01)

(52) U.S. Cl. ..................... 623/1.24; 623/1.25

(58) Field of Classification Search ...... 623/1.11–1.35, 623/1.2, 17.12, 1.36, 1.42, 1.3; 604/96.01
See application file for complete search history.

(56) References Cited

U.S. PATENT DOCUMENTS

| | | | |
|---|---|---|---|
| 3,657,744 A | 4/1972 | Ersek | |
| 4,300,244 A | 11/1981 | Bokros | |
| 4,409,172 A | 10/1983 | Ward, Jr. et al. | |
| 4,732,152 A | 3/1988 | Wallsten et al. | |
| 4,969,458 A | 11/1990 | Wiktor | |
| 5,078,726 A | 1/1992 | Kreamer | |
| 5,123,917 A | 6/1992 | Lee | |
| 5,151,105 A * | 9/1992 | Kwan-Gett | 623/1.25 |
| 5,156,620 A | 10/1992 | Pigott | |
| 5,282,824 A | 2/1994 | Gianturco | |
| 5,330,500 A | 7/1994 | Song | |
| 5,366,504 A | 11/1994 | Andersen et al. | |
| 5,383,926 A | 1/1995 | Lock et al. | |
| 5,387,235 A | 2/1995 | Chuter | |
| 5,389,106 A | 2/1995 | Tower | |
| 5,456,713 A | 10/1995 | Chuter | |
| 5,507,769 A | 4/1996 | Marin | |
| 5,507,771 A | 4/1996 | Gianturco | |
| 5,522,881 A | 6/1996 | Lentz | |
| 5,534,024 A | 7/1996 | Rogers et al. | |
| 5,554,119 A | 9/1996 | Harrison et al. | |

(Continued)

FOREIGN PATENT DOCUMENTS

DE 3902364 8/1989

(Continued)

OTHER PUBLICATIONS

Lawrence, Jr., D.D., Charnsangavej, C., Wright, K.C., Gianturco, C., and Wallace, S., Percultaneous Endovascular Graft: Experimental Evaluation. Radiology, 1986; 163:357-360.

(Continued)

*Primary Examiner*—Suzette J-J Gherbi
(74) *Attorney, Agent, or Firm*—Hoffmann & Baron LLP

(57) ABSTRACT

A tubular prosthesis is provided which includes a tubular member and an outer covering sealed to portions of the tubular member, with a pocket being defined therebetween. A filling agent, preferably a substantially incompressible agent, is disposed in the pocket so as to cause portions of the outer covering to expand from the tubular member. As an endovascular prosthesis, the filled pocket can be used as a seal against the wall of a blood vessel to prevent Type I endoleaks.

16 Claims, 6 Drawing Sheets

U.S. PATENT DOCUMENTS

| | | | | |
|---|---|---|---|---|
| 5,554,180 | A | * | 9/1996 | Turk ................... 623/1.25 |
| 5,562,726 | A | | 10/1996 | Chuter |
| 5,607,468 | A | | 3/1997 | Rogers et al. |
| 5,618,299 | A | | 4/1997 | Khosravi et al. |
| 5,665,117 | A | | 9/1997 | Rhodes |
| 5,693,088 | A | | 12/1997 | Lazarus |
| 5,725,547 | A | * | 3/1998 | Chuter ................ 606/194 |
| 5,735,892 | A | | 4/1998 | Myers et al. |
| 5,797,951 | A | | 8/1998 | Mueller |
| 5,824,038 | A | | 10/1998 | Wall |
| 5,824,054 | A | | 10/1998 | Khosravi et al. |
| 5,843,166 | A | | 12/1998 | Lentz et al. |
| 5,871,537 | A | * | 2/1999 | Holman et al. ........ 623/1.23 |
| 5,961,545 | A | | 10/1999 | Lentz et al. |
| 6,010,529 | A | | 1/2000 | Herweck et al. |
| 6,059,823 | A | * | 5/2000 | Holman et al. ........ 623/1.25 |
| 6,270,523 | B1 | | 8/2001 | Herweck et al. |
| 6,309,343 | B1 | | 10/2001 | Lentz et al. |
| 6,312,462 | B1 | * | 11/2001 | McDermott et al. ..... 623/1.25 |
| 6,319,276 | B1 | * | 11/2001 | Holman et al. ........ 623/1.25 |
| 6,391,002 | B1 | * | 5/2002 | Kokish ................ 604/96.01 |
| 6,395,019 | B2 | | 5/2002 | Chobotov |
| 7,033,389 | B2 | * | 4/2006 | Sherry ................ 623/1.42 |
| 2001/0027338 | A1 | | 10/2001 | Greenberg |
| 2003/0225453 | A1 | * | 12/2003 | Murch ................ 623/1.21 |

FOREIGN PATENT DOCUMENTS

| | | |
|---|---|---|
| EP | 0 657 147 | 6/1995 |
| EP | 0 689 805 | 1/1996 |
| EP | 0 737 453 | 10/1996 |
| SU | 1457 921 | 2/1989 |
| WO | WO 96/33672 | 10/1986 |
| WO | WO 95/02377 | 1/1995 |
| WO | WO 95/05132 | 2/1995 |
| WO | WO 95/29647 | 11/1995 |
| WO | WO 96/00103 | 1/1996 |
| WO | WO 96/10967 | 4/1996 |
| WO | WO 96/22745 | 8/1996 |
| WO | WO 96/28115 | 9/1996 |
| WO | WO 96/35577 | 11/1996 |
| WO | 00/51522 | 9/2000 |
| WO | WO 00/51522 | 9/2000 |
| WO | WO 01/21107 | 3/2001 |

OTHER PUBLICATIONS

Search Report issued on Jan. 21, 2003 for International Application No. PCT/US 02/30696.

* cited by examiner

AORTIC ARTERY ANEURYSM ENDOVASCULAR PROSTHESIS

FIELD OF THE INVENTION

This invention relates to tubular prostheses, including, but not limited to, endovascular grafts and stent/grafts, for maintaining patency of blood vessels and treating aortic artery aneurysms, and tubular conduits for maintaining patency in other bodily passageways.

BACKGROUND OF THE RELATED TECHNOLOGY

It is known in the prior art to use endovascular prostheses to treat aortic artery aneurysms ("AAA"). Such treatment includes implanting a stent, or stent/graft, within the diseased vessel to by-pass the anomaly. An aneurysm is a sac formed by the dilation of the wall of the artery, which may be congenital, but usually is caused by disease and, occasionally, by trauma. With reference to FIG. 1, sac 1 of aneurysm A is defined by dilated portions 2 of aortic artery AA. With the collection of blood and other embolic material in the sac 1, and being subjected to hemodynamic pressure, the aneurysm A may rupture, if untreated, causing internal bleeding.

Techniques had been developed in the prior art where diseased portions of a blood vessel, such as with an aneurysm, were ablated and replaced with a prosthetic member, such as that shown in U.S. Pat. No. 4,938,740 to Melbin. This technique, however, required open surgery. As an improvement over this technique, endovascular emplacement techniques have been developed to implant grafts and stent/grafts into a vessel from a remote puncture site, thereby obviating the need for open surgery. For example, as shown in FIG. 1, an endovascular prosthesis 3 (stent or stent/graft) is positioned to by-pass the aneurysm A with ends 4, 5 of the prosthesis being in contiguous contact with healthy portions of the aortic artery AA, the prosthesis 3 having been introduced endovascularly (e.g., with a catheter). Accordingly, if the aneurysm A was to rupture, blood flow through the aortic artery AA would be uninterrupted, and internal bleeding generally avoided.

Although considerable success has been enjoyed with stent and stent/graft performance, failures have been noted and predominantly classified in four classes: Types I–IV. Type I failures relate to leaks (referred to as endoleaks) between the vascular prosthesis and the vessel wall. For example, with reference to FIG. 1, a Type I failure would be blood weeping about the end 4 of the prosthesis 3 into the sac 1.

A Type II failure involves blood flowing into the aneurysm sac through collateral arteries. Again, with reference to FIG. 1, the sac 1 may be in fluid communication with blood vessels BV, other than the aortic artery AA. Typically, lumbar arteries are in fluid communication (directly or indirectly) with an aneurysm sac. Because blood flow out of the sac 1 is prevented, hemodynamic pressure away from the sac 1 is not present. However, because of hemodynamic pressure within blood vessels in communication with the sac 1, blood flow, nevertheless, is directed into the sac 1 (as shown by arrows). A technique has been developed in the prior art which calls for embolizing the blood vessels BV, such as with embolus coils, thereby isolating the sac 1 from collateral blood flow. However, an additional procedure would be required for embolization.

A Type III failure is a mechanical failure, wherein a hole may be ripped into the prosthesis (e.g., excessive wear at a metal/non-metal (fabric or polymer) interface) or poor integrity exists at a connection, or connections, between modular components of a prosthesis, (e.g., extensions may be connected to the prosthesis to obtain improved securement in one or both of the iliac arteries.) For example, as shown in FIG. 1, a hole 6 may be torn into the prosthesis 2, or poor sealing is obtained at the connection between the prosthesis 3 and an extension 7.

A Type IV failure relates to excessive prosthesis porosity, wherein blood seeps through the prosthesis regardless of the integrity of sealing and mechanical connections.

As can be readily appreciated, even with the successful implantation of an endovascular prosthesis, failures may occur thereafter. It has been found that Type I failures may effect up to 5–10% of all implanted prostheses. Accordingly, there is a clear need for an endovascular prosthesis which can reduce the likelihood of, and ideally eliminate, Type I failures.

SUMMARY OF THE INVENTION

To overcome deficiencies in the prior art, a tubular prosthesis is provided that includes a tubular member and an outer covering sealed to portions of the tubular member, with a pocket being defined therebetween. A filling agent, preferably a substantially incompressible agent, is disposed in the pocket so as to cause portions of the outer covering to extend from the tubular member. In one aspect of the invention, the prosthesis may be an endovascular prosthesis. Advantageously, the filled pocket can be used as a seal against the wall of a blood vessel to prevent Type I endoleaks. Preferably, the pocket is annular shaped, with a seal ring being formed upon the pocket being filled with the agent. This invention is particularly beneficial in sealing a blood vessel having partial blockage (e.g., aortic calcification) and/or irregular vessel cross-sectional shape (e.g., neck angulation).

Preferably, the agent is disposed in the pocket subsequent to the implantation of the prosthesis. In one aspect of the invention, a fluid conduit is placed into fluid communication with the pocket prior to implantation of the prosthesis in the human body. The agent is injected into the pocket via the fluid conduit. Thereafter, it is desirable that the fluid conduit be detached and withdrawn with any other deployment device, such as a guidewire.

The tubular member may be of any endovascular prosthetic construction known in the prior art, including graft and stent/graft configurations. The tubular member may be a textile graft, a polymeric graft, or a combination thereof (single layer or multi-layer). In addition, the tubular member may have a stent reinforcement (a single stent or multiple stents), such stent being self-expanding or expandable by a distensible member, such as a balloon. It is desirable that the tubular member be impervious to the agent, at least at locations defining the pocket, to prevent transmission therethrough of the agent.

The outer covering may be formed of a textile material, a polymeric material (optionally elastomeric), or a combination thereof. It is preferred that the outer covering be expandable so as to allow for increase in the volume of the pocket upon filling with the agent. The outer covering may also be formed to be pervious or impervious to the transmission therethrough of the agent. For example, where it is desired to have the outer covering be impervious to the agent to prevent transmission of the agent into the sac of the aneurysm being treated, the outer covering may be formed from compliant latex material, such as that commonly used with distensible balloons. If it is desired to have the outer covering be pervious, it may be formed of a textile material, such as a knit polyester, which would allow the agent to at least partially transmit therethrough.

The agent is preferably injected into the pocket in liquid form and solidified therein as a flexible elastomer. The agent may be formed of hydrogels, moisture activated urethanes, and cyanoacrylates. If two-part fluid systems are used to solidify the agent (e.g., such as with cross-linking epoxies or two-part surgical sealants), two or more fluid conduits (as required) may be used to introduce the liquids into the pocket. The agent may be a fluid, a semisolid matter (e.g., a gel), or a solid. It is preferred that the agent be substantially incompressible once in the pocket and in use.

The tubular prosthesis may be used as an endovascular prosthesis, as well as, in other applications to maintain patency of a bodily passageway, such as the esophagus, trachea, colon, biliary tract, urinary tract, prostate, and brain.

These and other features of the invention will be better understood through a study of the following detailed description and accompanying drawings.

DETAILED DESCRIPTION OF THE INVENTION

Figure 1:
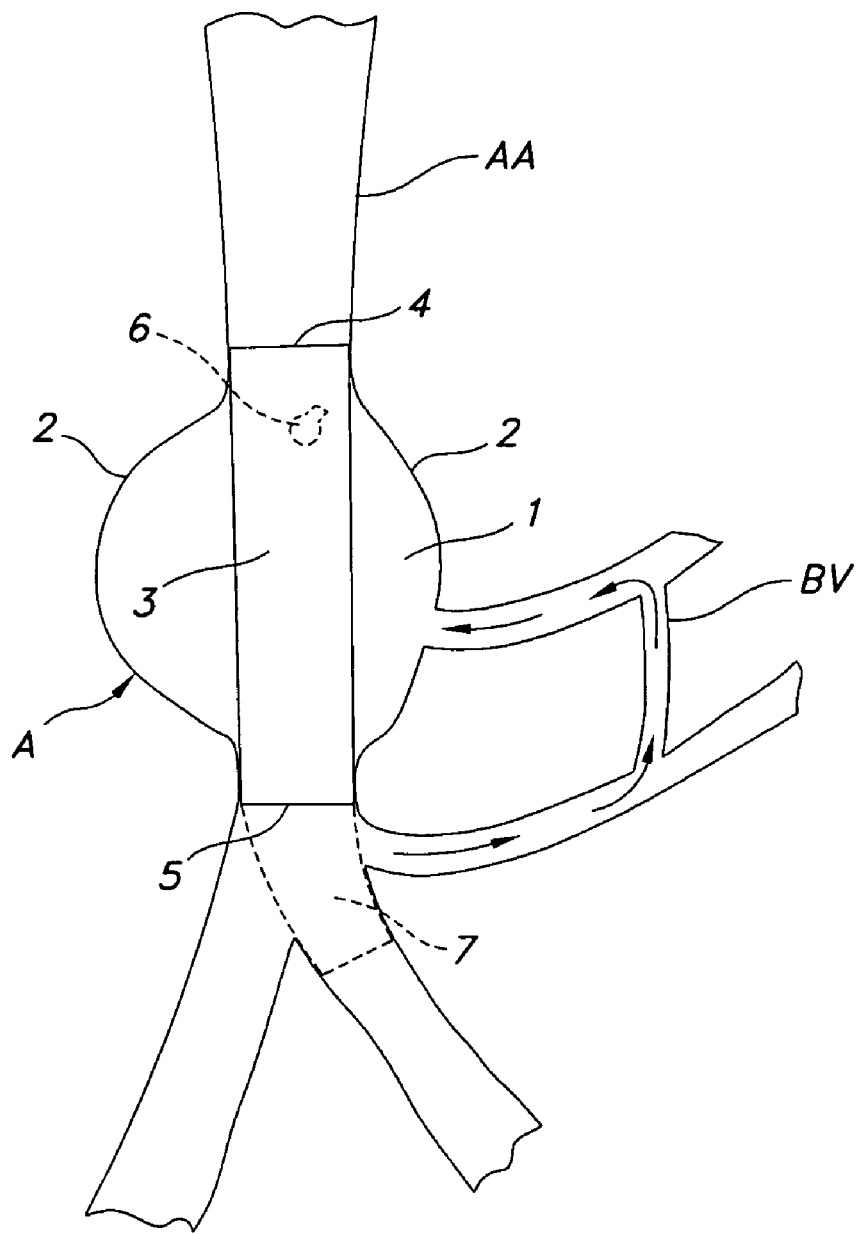
FIG. 1 is a schematic of a prior art endovascular prosthesis positioned to by-pass an aortic artery aneurysm (AAA)
Figure 2:
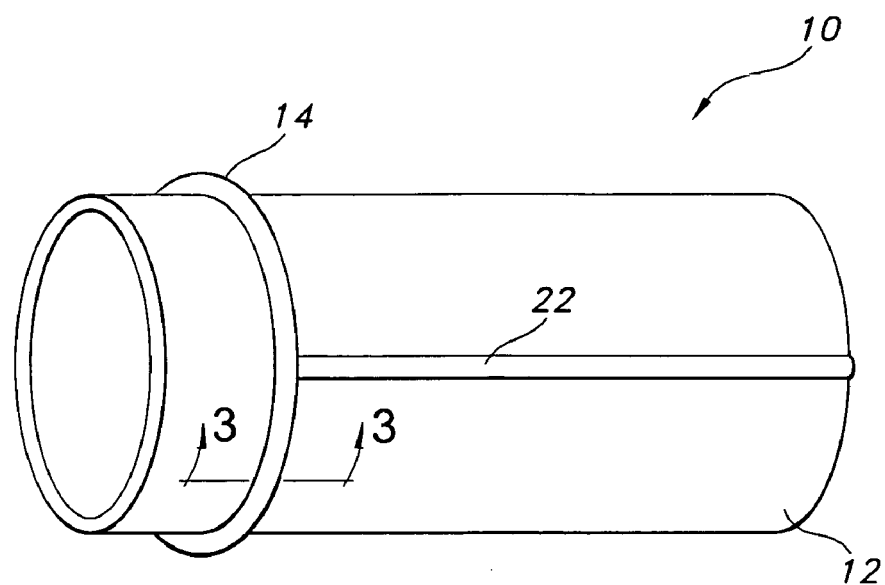
FIG. 2 shows a first embodiment of a tubular prosthesis formed in accordance with the subject invention.

With reference to FIG. 2, a first embodiment of an endovascular prosthesis is shown and designated with the reference numeral 10. Reference will be made herein to the prosthesis being endovascular, although as pointed out above, the prosthesis may be used in other applications. The prosthesis 10 generally includes a tubular member 12 and an outer covering 14 sealed to portions of the tubular member 12 so as to define a pocket 16 therebetween. A filling agent 18, which is preferably substantially incompressible, is disposed in the pocket 16 so as to at least partially fill the pocket 16 and cause it to extend from the tubular member 12. With the pocket 16 being at least partially filled by the filling agent 18, the filled pocket 16 may press against a portion or portions of the wall of a blood vessel to act as a seal thereagainst. Consequently, the seal may be used to reduce the likelihood of Type I endoleaks.

The tubular member 12 may be of any endovascular prosthetic construction known, such as being a stent or a stent/graft. Any material commonly used in the formation of endovascular prostheses may also be used, such as textiles, polymeric materials, or a combination thereof. Single or multiple layers may also be used. It is preferred that the tubular member 12 be impervious to the transmission therethrough of the filling agent 18. Accordingly, exposure of the filling agent 18 to the blood stream may be avoided.

Figure 6:
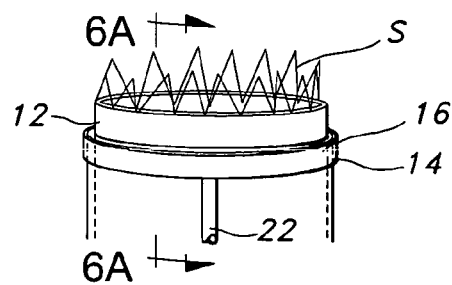
FIG. 6 shows an unexpanded seal ring.
Figure 7:
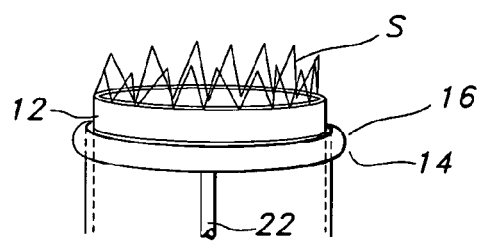
FIG. 7 shows an expanded seal ring.
Figure 10:
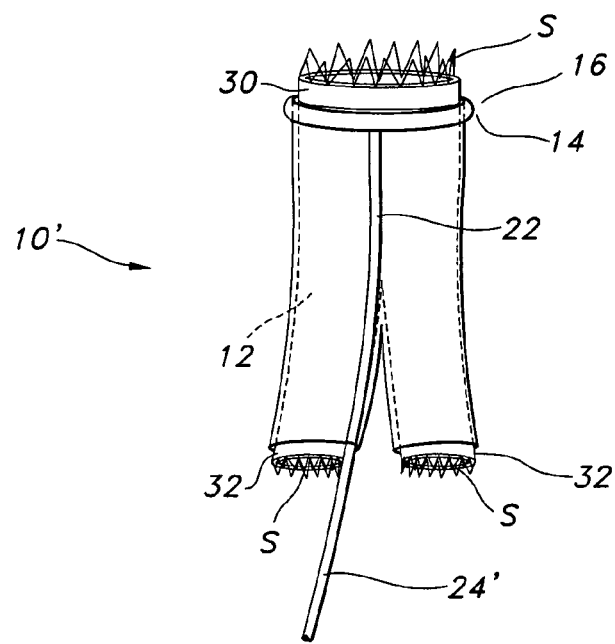
FIG. 10 shows a second embodiment of a prosthesis formed in accordance with the subject invention; and, FIG. 11 is a partial cross-sectional view showing a cuffed construction.

If the tubular member 12 is a stent/graft, any stent known in the art may be used, including, but not limited to, self-expanding stents and expandable stents, which can be expanded by a distensible member, such as a balloon. Single or multiple stents may also be used. FIGS. 6, 7 and 10 show stents S in use with the subject invention.

Figure 3:
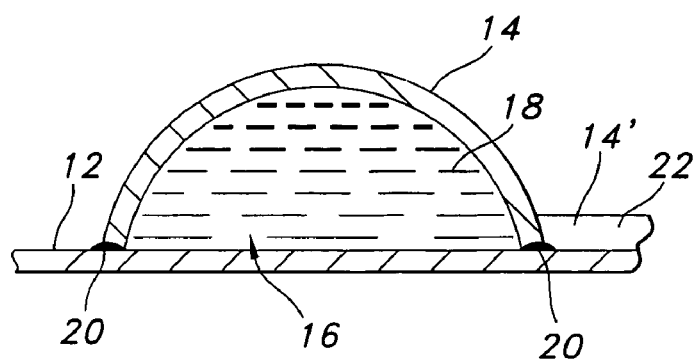
FIG. 3 is a partial cross-sectional view taken along line 3—3 of FIG. 2.
Figure 4:
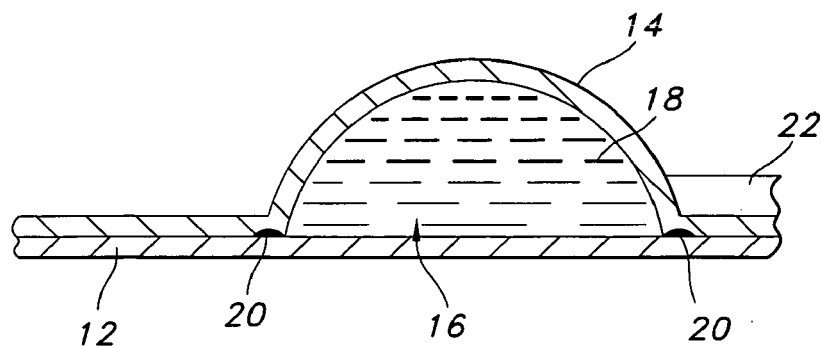
FIG. 4 is a partial cross-sectional view, similar to FIG. 3, but showing a different construction.

The outer covering 14 is sealed to portions of the tubular member 12 using any technique known to those skilled in the art, including, but not limited to, bonding and fusing. As shown in FIG. 3, sealed portions 20 preferably bound a pocket 16 so as to retain the filling agent 18 therein. With reference to FIG. 3, the outer covering 14 may be formed to the dimensions of the pocket 16 (i.e., not extend beyond the sealed portions 20). Alternatively, as shown in FIG. 4, the outer covering 14 may extend beyond the dimensions of the pocket 16 such as, for example, to be coextensive with the tubular member 12. With this variation, the sealed portions 20 of the outer covering 14 again bound the pocket 16 so as to retain the filling agent 18 therein.

Figure 6A:
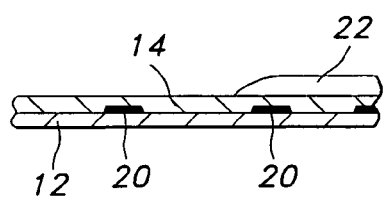
FIG. 6A is a partial cross-sectional view taken along line 6A—6A of FIG. 6.

It is preferred that the pocket 16 be expandable so that the endovascular prosthesis 10 may be implanted with the pocket 16 in an unexpanded state and having a generally low profile (preferably flat profile), as shown in FIG. 6A. Accordingly, the pocket 16 will minimally hinder the implantation process. Yet, with the ability to expand, the pocket 16 is able to accommodate an effective amount of the filling agent 18 in an expanded state, as shown in FIG. 7.

Where it is desired to have the outer covering 14 be impervious to the transmission therethrough of the filling agent 18, the outer covering 14 may be formed from a polymeric material or an elastomeric material, such as compliant latex material which is commonly used with distensible balloons. If it is desired to have the outer covering 14 be at least partially pervious to the transmission therethrough of the filling agent 18, it may be formed of a textile material, such as a knit polyester. Other materials are possible. It should be noted that pervious polymeric and/or elastomeric materials may be utilized (e.g., expanded polytetrafluoroethylene), or, impervious textile materials, which, for example are treated with sealant materials. It should also be noted that the filling agent 18 may include various multiple components, such as, for example, a gel material to fill the pocket 16 and a therapeutic agent such as those used for treating an aneurysm. If so, the outer covering 14 may be formed impervious to certain component(s) of the filling agent 18 (e.g., the gel material), while being pervious to other components (e.g., the liquid therapeutic agent). Clearly, the viscosity of the components largely affects the ability to have controlled transmission. It is preferred that the outer covering 14 be impervious to the filling agent 18.

Non-limiting examples of therapeutic agents which may be incorporated with the filling agent include: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promoters); vascular cell growth inhibitors (such as growth factor inhibitors, growth factor receptor F antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

One manner of facilitating expansion of the pocket 16 is through the selection of a stretchable material for forming the outer covering 14. In addition, the constituent material of the tubular member 12 may also be selected to be stretchable so as to allow for expansion of the pocket 16. It must be noted, however, that it is desired to have the pocket 16 fill in a radially outwardly direction. Thus, it is preferred that the tubular member 12 be formed to allow for minimal (ideally no) inward expansion of the pocket 16.

Figure 6B:
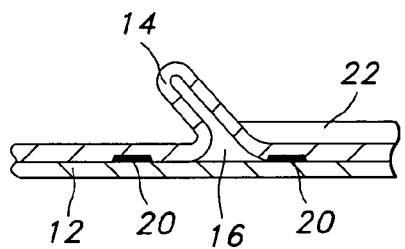
FIG. 6B is a partial cross-sectional view, similar to FIG. 6A, but showing a pleated construction.

The outer covering 14 may also be provided with excess material to allow for the expansion of the pocket 16, such as by forming the outer covering 14 as a pleat, as shown in FIG. 6B. It is preferred that the outer covering 14 be both formed of a stretchable material, as well as being formed with excess material in the form of a pleat. An excessively large pleat may give the pocket 16 a non-flat profile during implantation. Thus, the inherent ability of the outer covering 14 to stretch allows for the outer covering 14 to be formed as a relatively smaller pleat.

As shown in FIG. 2, it is desirable that the pocket 16 be annular-shaped so as to form a seal ring about the endovascular prosthesis 10. In addition, it is preferred that the pocket 16 be located closer to the upstream end of the endovascular prosthesis 10 relative to blood flow. In this manner, the pocket 16 may limit the extent to which blood may weep about the tubular member 12.

The filling agent 18 is preferably introduced into the pocket 16 in liquid form and solidified therein. Desirably, the solidified form is a flexible elastomer. Crosslinking, as well as non-crosslinking materials may be employed. Materials which are hydrogels or behave similarly to hydrogels are useful. The filling agent 18 may be formed of hydrogels, moisture activated urethanes, cyanoacrylates, as well as other materials which are capable of providing sufficient expansion of the pocket 16 for sealing. It is preferred that the filling agent 18 be introduced into the pocket 16, once the endovascular prosthesis 10 is implanted in the desired location. In one aspect of the invention, a channel 22 extends from an end of the tubular member 12 and into fluid communication with the pocket 16. The channel 22 may be formed in similar fashion to the pocket 16, although the channel 22 can be formed with smaller dimensions. For example, as shown in FIG. 3, the channel 22 may be formed from a secondary outer covering 14' which is sealed to portions of the tubular member 12 in the same manner as the outer covering 14. Alternatively, with reference to FIG. 4, where the outer covering 14 extends beyond the pocket 16, the channel 22 may also be defined by the outer covering 14 by selectively sealing portions thereof.

To facilitate efficient filling of the pocket 16, the pocket 16 may be vented (one or more vent holes formed in communication with the pocket 16); and/or evacuated prior to, and/or while, filling (e.g., via the channel 22). These procedures can be avoided by forming the outer covering 14 of compliant material which expands upon filling of the pocket 16.

As a further variation, the channel 22 may be a tube (e.g., a microcatheter) which is bonded or fused to portions of the tubular member 12. As a tube, the channel 22 may be exposed (as shown in FIG. 3) or at least partially covered by the outer covering 14 where the outer covering 14 extends beyond the pocket 16.

Figure 5A:
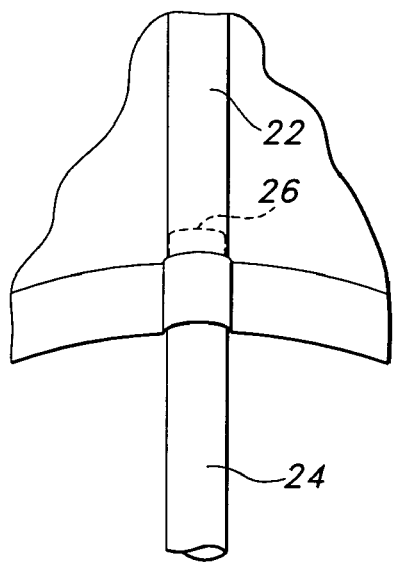
FIGS. 5A and 5B show different methods of connecting a fluid conduit to the prosthesis.
Figure 5B:
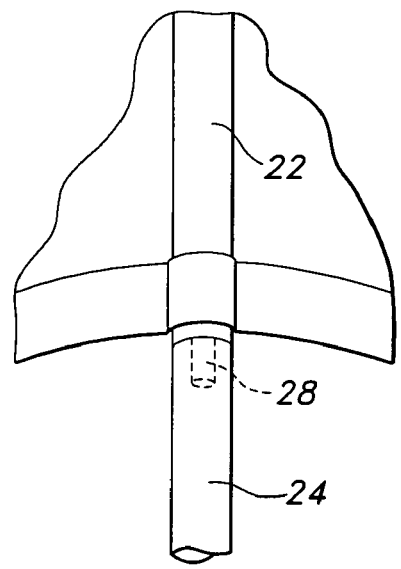

To introduce the filling agent 18, it is preferred that a fluid conduit 24 be placed into fluid communication with the channel 22, as shown in FIGS. 5A and 5B. Referring to FIG. 5A, the fluid conduit 24 may be in direct fluid communication with the channel 22, wherein an end 26 of the fluid conduit 24 is located within the channel 22. Alternatively, as shown in FIG. 5B, the fluid conduit may be in indirect communication with the channel 24 via valve (preferably one-way) 28. Various valve/conduit constructions are contemplated. For example, the construction of the valve 28 and the fluid conduit 24 may be the same as or similar to that used with silicone balloon distension (e.g., the system sold under the trademark "APOLLO" by Target Therapeutics of Fremont, Calif.). Once the fluid conduit 24 has conveyed the filling agent 18 into the channel 22, it is preferred that the fluid conduit 24 be detached and withdrawn from the body. Thus, as can be appreciated, with the type of connection shown in FIG. 5A (direct fluid communication), the channel 22 will be open and exposed upon detachment of the fluid conduit 24. It is preferred to only use this type of connection where the filling agent 18 will be sufficiently solidified and/or have sufficient viscosity to not leak out of the channel 22.

In use, the endovascular prosthesis 10 is implanted using any technique known. For example, a Strecker type drawstring deployment system may be employed with the subject invention, such as that disclosed in U.S. Pat. No. 5,405,378, the disclosure of which is incorporated by reference herein. Desirably, the fluid conduit 24 is attached to the endovascular prosthesis 10 prior to insertion into the human body. Once implanted, an effective amount of the filling agent 18 is injected via the fluid conduit 24 and the channel 22 into the pocket 16 so as to cause at least partial expansion thereof. Once the effective amount of the filling agent 18 has been introduced, the fluid conduit 24 is caused to be detached, preferably by a pull or a push of an outer catheter sleeve, and withdrawn with any other deployment device, such as an introducer catheter. The filling agent 18 solidifies and defines a seal ring which is in at least partial contiguous contact with the wall of the blood vessel to limit, and ideally altogether prevent, Type I endoleaks. It is preferred that the filling agent 18 be substantially incompressible so as to maintain its sealing effect.

Figure 8:
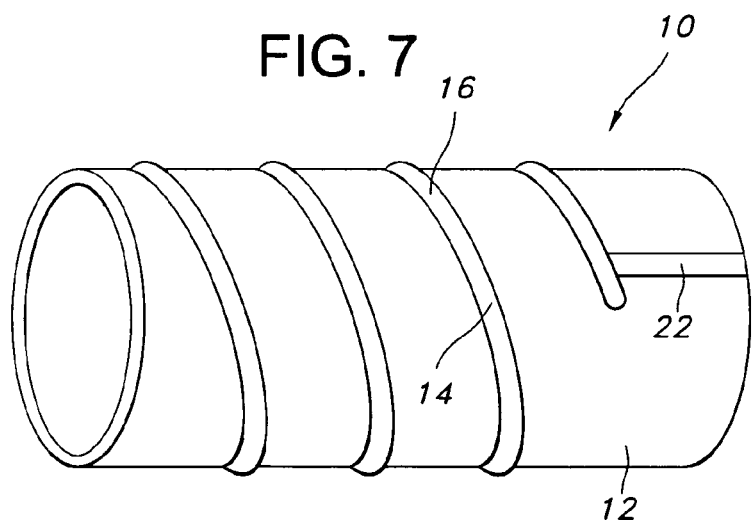
FIGS. 8 and 9 show different pocket configurations.
Figure 9:
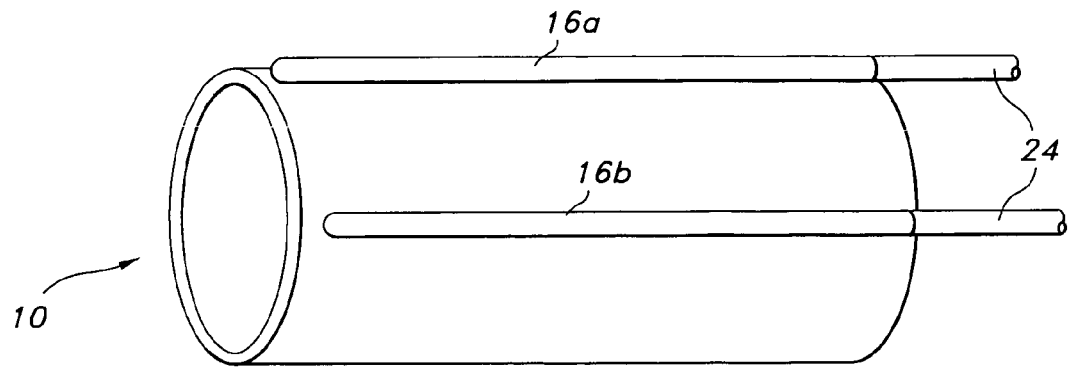

As those skilled in the art will recognize, the subject invention can be modified in various ways in accordance with the teachings herein to have different pocket shapes and/or multiple pockets. For example, as shown in FIGS. 8 and 9, the endovascular prosthesis 10 may have a helical pocket 16 or multiple pockets 16a, 16b. As shown in FIG. 8, the pocket 16 may be helical so as to not only provide a sealing effect for the prosthesis 10, but also provide structural support for the tubular member 12 (i.e., kink resistance). Likewise, multiple pockets 16a, 16b may be utilized to also provide structural support. If multiple pockets 16, 16a are to be utilized, multiple fluid conduits 24 may be required to convey filling agent to each one of the multiple pockets 16a, 16b, or, alternatively, although not shown, a single fluid conduit 24 may be connected to a manifold which feeds the multiple pockets 16a, 16b. Other shapes and arrangements are possible.

Furthermore, multiple fluid conduits 24 may be required to inject fluid into a single pocket 16 such as if a two-part fluid system is used to solidify the agent as with crosslinking epoxies or two-part surgical sealants.

With reference to FIG. 10, a second embodiment of the subject invention is shown, wherein the endovascular prosthesis 10' is formed with a Y-shape, i.e., bifurcated form, having a main body 30 from which extend two branches 32. The endovascular prosthesis 10' may be used in the aortic artery, with the branches 32 extending into the iliac arteries. Here, it is preferred to have the pocket 16 be located in proximity to the end of the main body 30, which is the upstream end of the prosthesis 10' relative to blood flow. In all respects, the endovascular prosthesis 10' is formed and operates with the same principles described above with respect to the endovascular prosthesis 10. Other shapes of the endovascular prosthesis, such as tapered, stepdown, and varying diameter prostheses, are useful and possibly can be used.

Furthermore, one or more of the pockets 16 may be located in proximity to modular components (such as extension 7 discussed above) connected to the endovascular prosthesis 10, 10' to improve the sealing effect in proximity to the juncture of the modular component and the prosthesis 10, 10'. Additionally, the modular component may be formed with one or more of the pockets 16. The pocket 16 can be used to form a seal with any other conduit, be it a bodily passageway, and/or a secondary prosthetic component.

Figure 11:
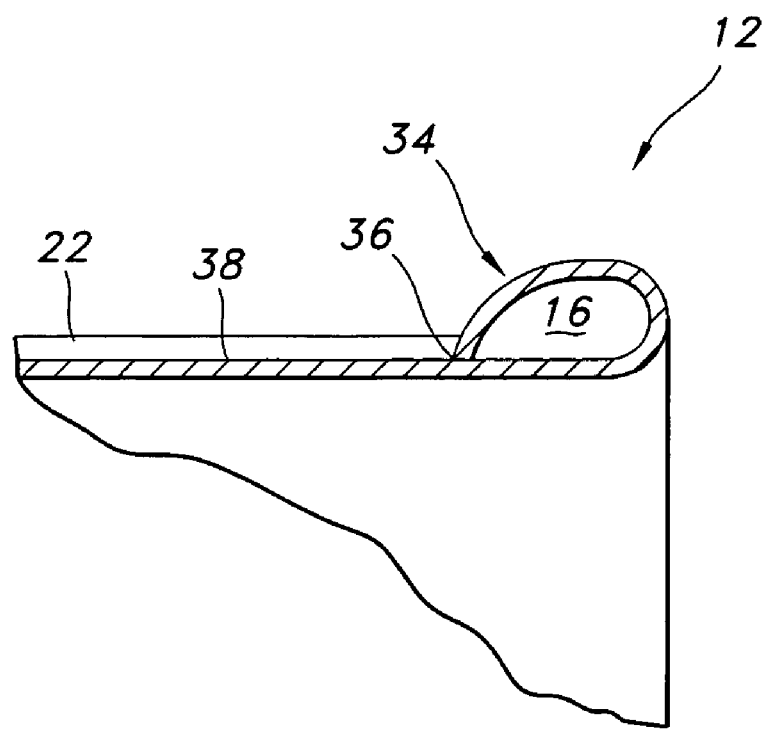

As further variations, the pocket 16 can be at least partially defined by folding portions of the tubular member 12, 12' and forming one or more cuffs 34, as shown in FIG. 11. By way of example, as shown in FIG. 11, edge 36 of tubular member 12 is fixed to a tubular portion 38 thereof using any conventional technique, such as bonding or fusing, but may also be sewn. Accordingly, the cuff 34 defines an enclosed pocket 16. The material of the cuff 34 may be formed in the same manner as the outer covering 14 described above. Alternatively, although not shown, the outer covering 14 may be knitted or woven with the tubular member 12, 12' and, thus, be integrally formed together. With the tubular member 12, 12' being preferably impervious to the filling agent 18 (and/or other agents, such as therapeutic drugs), the cuff 34 and the integrally-formed outer covering 14 are advantageously formed impervious. These alternative embodiments are practiced in accordance with the teachings disclosed above.

Various changes and modifications can be made in the present invention. It is intended that all such changes and modifications come within the scope of the invention as set forth in the following claims.

What is claimed is:

1. A prosthesis comprising: a an implantable tubular member; and an outer covering sealed to portions of said tubular member, a pocket being defined between said tubular member and said outer covering to accommodate a pre-determined agent, said outer covering being impervious to said pre-determined agent and being pleated about said pocket, wherein said pocket is formed to be expandable with said outer covering being pleated about said pocket.

2. A prosthesis as in claim 1, wherein said tubular member is a graft.

3. A prosthesis as in claim 1, wherein said tubular member is a stent/graft combination.

4. A prosthesis as in claim 3, wherein said stent is expandable.

5. A prosthesis as in claim 4, wherein said stent is self-expanding.

6. A prosthesis as in claim 1, wherein said outer covering is pervious to a therapeutic agent disposed in said pocket.

7. A prosthesis as in claim 1, wherein said tubular member is impervious to said pre-determined agent.

8. A prosthesis as in claim 1, wherein said pre-determined agent is substantially incompressible.

9. A prosthesis as in claim 1, wherein said pre-determined agent is a fluid.

10. A prosthesis as in claim 1, wherein said pre-determined agent is in a semisolid state.

11. A prosthesis as in claim 1, wherein said outer covering is formed of a stretchable material.

12. A prosthesis as in claim 1, further comprising a fluid conduit in fluid communication with said pocket.

13. A prosthesis as in claim 12, wherein said fluid conduit is in fluid communication with said pocket via a channel.

14. A prosthesis as in claim 1, wherein said tubular member has a first end, said pocket being located in proximity to said first end.

15. A prosthesis as in claim 1, wherein said prosthesis is an endovascular prosthesis.

16. A tubular prosthesis comprising: a tubular member, and an outer covering sealed to portions of said tubular member, a pocket being defined between said tubular member and said outer covering to accommodate a pre-determined agent, said outer covering being impervious to said pre-determined agent, wherein said outer covering is pervious to a therapeutic agent disposed in said pocket.

* * * * *

UNITED STATES PATENT AND TRADEMARK OFFICE
CERTIFICATE OF CORRECTION

| | | |
|---|---|---|
| PATENT NO. | : 7,192,441 B2 | Page 1 of 1 |
| APPLICATION NO. | : 09/978383 | |
| DATED | : March 20, 2007 | |
| INVENTOR(S) | : John E. Sherry | |

It is certified that error appears in the above-identified patent and that said Letters Patent is hereby corrected as shown below:

Column 8, Claim 1, line 10, replace "comprising a an implantable" with --comprising an implantable--.

Signed and Sealed this

Twenty-second Day of May, 2007

JON W. DUDAS
*Director of the United States Patent and Trademark Office*